United States Patent [19]

Klemm

[11] Patent Number: Plant 7,153

[45] Date of Patent: Feb. 13, 1990

[54] GERANIUM PLANT NAMED MARKTEX

[76] Inventor: Siegfried Klemm, Hanfacker 8, D-7000 Stuttgart 50, Fed. Rep. of Germany

[21] Appl. No.: 262,331

[22] Filed: Sep. 12, 1988

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Charles W. Rummler

[57] ABSTRACT

A new and distinctive geranium cultivar particularly distinguished by its very large flower clusters, or flower balls, of a light red or vermilion coloration and comprising up to about sixty closely-growing florets of medium size, each with five very broad, imbricated petals. The cluster stalks are sturdy, upright, brown in color and about 12 cm. long and the blooms are very long lasting. The foliage is bushy and abundant, the medium sized leaf having an intensive zonation, and the foliage extends about 15 cm. above the soil.

1 Drawing Sheet

BACKGROUND OF THE NEW PLANT

This new geranium cultivar originated as a seedling of a random pollinated variety named 'Osna' (unpatented) being grown in my nursery at Stuttgart, West Germany, with the object of seed collection. The present variety was selected for propagation from a group of seedlings of 'Osna' because of the very large size and light red coloration of its flower clusters, which comprise about sixty closely-growing florets, the petals of which have a pleasing red body color and lightly colored marginal edges; and because of its abundant, sturdy foliage of dark green, medium sized leaves which offset the color intensity of the flowers, propagation of this selected plant was carried on by me and under my direction by means of cuttings at Stuttgart with such success that propagation was continued at Stuttgart in the same manner through several successive generations, which demonstrated conclusively that the distinctive characteristics of the selected plant would hold true from generation to generation and appeared to be firmly fixed. This new plant is now being propagated by means of cuttings for commercial purposes at Stuttgart.

DESCRIPTION OF THE DRAWING

My new geranium cultivar is illustrated by the accompanying photographic drawing which, in full color, shows several clusters of florets and buds with the color rendition being as closely true to that herein specified as is reasonably possible to obtain by conventional, professional, photographic procedures.

DESCRIPTION OF THE NEW PLANT

The following is a detailed description of my new geranium cultivar as observed in nursery at Stuttgart in the Spring of 1988, with color designations according to The R.H.S. Colour Chart of The Royal Horticultural Society of London, England.

THE PLANT

Origin: Seedling.

Parentage:

*Seed parent.*—The variety 'Osna' (unpatented).

*Pollen parent.*—Unknown.

Classification:

*Botanic.*—*Pelargonium zonale* Hybrid.

*Commercial.*—Geranium.

Form: Compact and very bushy.

Height: About 25 cm.

Branching character: Very good.

Growth habit: Upright and compact, with good strength and a medium growth habit.

Flower stem length: About 12 to 15 cm.

Foliage:

*Quantity.*—Abundant.

*Size of leaf.*—About 7 cm. wide and 6 cm. long.

*Leaf shape.*—Reniform with crenate margins.

*Texture.*—Smooth.

*Color.*—Upper side — Dark green with a lighter green in the middle part and intensive zonation. Under side — Medium green.

*Ribs and veins.*—The leaf has four, light green main veins.

THE BUD

Size: Normal.

*Diameter.*—About 8 mm.

*Length.*—About 17 mm.

Form: Generally narrow elliptic with ovoid body and pointed tip.

Rate of opening: Medium.

Color of Floret petals: When sepals first divide, light salmon to white. When petals begin to unfurl, salmon.

Sepals:

*Number.*—Five.

*Shape.*—Lanceolate.

*Character.*—The sepals stand up when the flowers open.

*Color.*—Inside — Green. Outside — Dark green.

Calyx:

*Shape.*—Flat, and wide open with no splitting.

Cluster stalk:

*Length.*—About 12 cm.

*Color.*—Brown.

*Character.*—Sturdy, erect and rigid.

THE INFLORESCENCE

Blooming habit: Continuous from early Spring through late midseason.

Blooms: Moderate in number.

Cluster size: Very large.

*Diameter.*—About 12 to 13 cm.

*Depth.*—Between florets, about 10 cm.

Florets:

*Size.*—Small. Diameter — About 4.5 cm. Depth — About 1.5 cm.

*Number.*—Up to about sixty.

*Borne.*—Singly on a stem of the umbel-formed cluster.

*Shape.*—When bloom first opens, cup-shaped. When bloom matures, flat cup.

*Petalage.*—Number: Five. Arrangement: Imbricated. Form: Very broad with rounded apex and entire margins. Texture: Soft. Aspect: Satiny. Color: Vermilion, RHS 41-B.

Cluster stalk:

*Length.*—About 12 cm.

*Color.*—Brown.

*Character.*—Upright and very strong.

Persistence: Very long; the petals stay on the plant for about sixteen or seventeen days.

Disease resistance: Resistant to Botrytis as observed in the Stuttgart area of West Germany.

REPRODUCTIVE ORGANS

Stamens:

*Number.*—Seven.

*Arrangement.*—A ring around the ovary.

*Anthers.*—Size: 2 mm. Color: Dark orange to red.

*Filaments.*—Number: One. Style: Length: About 5 to 6 mm. Stigma: Five cells. Color: Like orange glass.

*Ovaries.*—Normal.

THE FRUIT

Fertility: The fruit is fertile.

Shape: Ovoid.

Color at maturity: Dark brown.

This new geranium cultivar has very beautiful and simple but intensive salmon-colored flowers as they appear over the dark foliage of the brush providing a special contrast between the clear salmon-colored, long lasting flower and the dark foliage, and has good resistance against Botrytis in wet summers.

I claim:

1. The new and distinctive geranium cultivar, substantially as herein shown and described, characterized in particular by the very large size of the umbel-formed flower clusters of about twelve, dark salmon-colored florets, each of which has broad, closely imbricated petals, and by its abundant foliage of medium sized, dark green leaves.

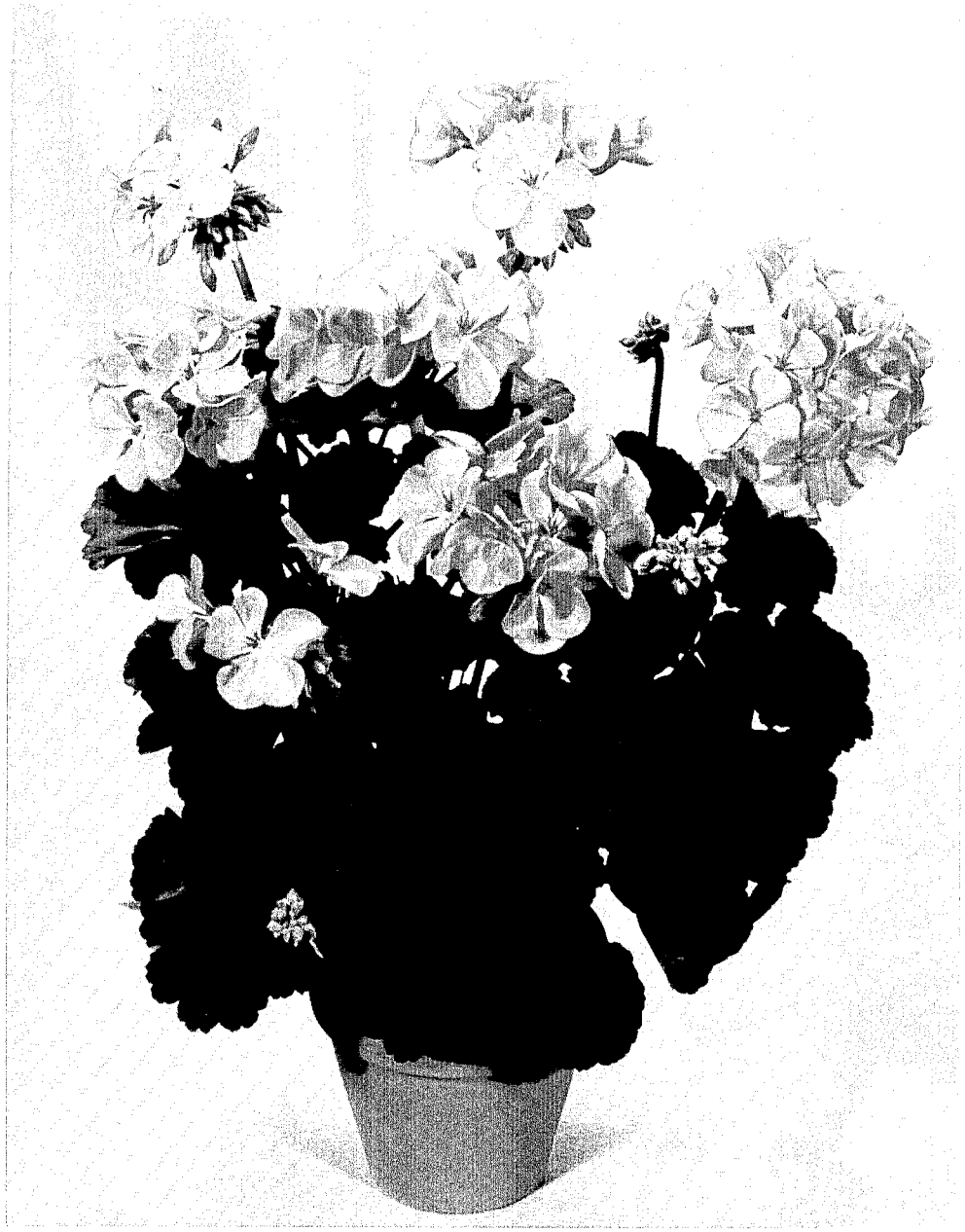

* * * * *